(12) United States Patent
Yamazaki et al.

(10) Patent No.: US 7,679,031 B2
(45) Date of Patent: Mar. 16, 2010

(54) METHOD FOR CHECKING A NOZZLE FOR A LASER BEAM MACHINE

(75) Inventors: Tsunehiko Yamazaki, Aichi pref. (JP); Naoomi Miyakawa, Aichi pref. (JP)

(73) Assignee: Yamazaki Mazak Corporation, Aichi pref. (JP)

( * ) Notice: Subject to any disclaimer, the term of this patent is extended or adjusted under 35 U.S.C. 154(b) by 625 days.

(21) Appl. No.: 11/121,660

(22) Filed: May 4, 2005

(65) Prior Publication Data

US 2005/0263510 A1  Dec. 1, 2005

(30) Foreign Application Priority Data

May 26, 2004  (JP) .............................. 2004-155930

(51) Int. Cl.
  *B23K 26/00* (2006.01)
  *B23K 26/02* (2006.01)
(52) U.S. Cl. ................................................. 219/121.83
(58) Field of Classification Search ..............................
  219/121.63–121.72, 121.83
  See application file for complete search history.

(56) References Cited

U.S. PATENT DOCUMENTS

| | | | | |
|---|---|---|---|---|
| 3,745,321 | A | * | 7/1973 | Shapiro et al. .......... 219/121.36 |
| 4,255,762 | A | * | 3/1981 | Takeyasu et al. .............. 348/84 |
| 5,171,963 | A | * | 12/1992 | Saruta et al. ........... 219/121.69 |
| 5,229,572 | A | * | 7/1993 | Ito ......................... 219/121.67 |
| 5,662,822 | A | * | 9/1997 | Tada et al. ............. 219/121.67 |
| 5,717,187 | A | * | 2/1998 | Rogozinski et al. .... 219/121.54 |
| 5,742,396 | A | * | 4/1998 | Kazem-Goudarzi et al. . 356/394 |
| 5,828,448 | A | * | 10/1998 | Jakobsen et al. ......... 356/237.1 |
| 5,838,840 | A | * | 11/1998 | King et al. .................. 382/300 |
| 5,850,469 | A | * | 12/1998 | Martin et al. ................ 382/154 |
| 5,854,460 | A | | 12/1998 | Graf et al. |
| 5,883,437 | A | * | 3/1999 | Maruyama et al. .......... 257/773 |
| 5,925,155 | A | * | 7/1999 | Rodgers ....................... 55/282 |
| 5,972,515 | A | * | 10/1999 | Murayama et al. ........ 428/425.9 |
| 6,025,571 | A | * | 2/2000 | Walters et al. ......... 219/121.67 |
| 6,030,276 | A | * | 2/2000 | Mortell et al. .................. 451/5 |

(Continued)

FOREIGN PATENT DOCUMENTS

EP  1 211 015 A1  6/2002

(Continued)

OTHER PUBLICATIONS

Chinese Office Action for corresponding Application No. 200510073897.1 dated Dec. 21, 2007 (with English Translation).

(Continued)

*Primary Examiner*—Samuel M Heinrich
(74) *Attorney, Agent, or Firm*—Renner, Otto, Boisselle & Sklar, LLP (57) ABSTRACT

The invention provides a device which optically checks a nozzle tip of a laser machining tool. A camera unit 450 which is raised and lowered in opposing relation to a nozzle 65 of a laser beam machine has a camera chamber 454 and is sealed by protective glass 456, where the camera chamber 454 contains a CCD camera body 460 and lens 462. While a ring light 470 illuminates a surface of the nozzle 65, the CCD camera body 460 checks the nozzle 65 optically.

6 Claims, 14 Drawing Sheets

U.S. PATENT DOCUMENTS

| | | | |
|---|---|---|---|
| 6,097,020 A | 8/2000 | Karasaki | |
| 6,181,411 B1 * | 1/2001 | Harris et al. | 356/4.01 |
| 6,225,589 B1 * | 5/2001 | Bartok | 219/69.15 |
| 6,324,255 B1 * | 11/2001 | Kondo et al. | 378/119 |
| 6,385,290 B1 * | 5/2002 | Kondo et al. | 378/84 |
| 6,818,857 B1 * | 11/2004 | Cho et al. | 219/121.64 |
| 7,012,689 B2 * | 3/2006 | Sharpe | 356/399 |
| 2007/0023405 A1 * | 2/2007 | Diem | 219/121.84 |
| 2008/0296799 A1 * | 12/2008 | Faubel et al. | 264/166 |

FOREIGN PATENT DOCUMENTS

| | | | |
|---|---|---|---|
| EP | 1250975 | | 10/2002 |
| JP | 359079831 A | * | 5/1984 |
| JP | 362292295 A | * | 12/1987 |
| JP | 401078692 A | * | 3/1989 |
| JP | 401138445 A | * | 5/1989 |
| JP | 402229690 A | * | 9/1990 |
| JP | 406163386 A | * | 6/1994 |
| JP | 406344163 A | * | 12/1994 |
| JP | 08113816 A | * | 5/1996 |
| JP | 408197268 A | * | 8/1996 |
| JP | 10-314969 | | 2/1998 |
| JP | 10-258376 | | 9/1998 |
| JP | 11033772 A | * | 2/1999 |
| JP | 2001179437 A | * | 12/1999 |
| JP | 02001304819 A | * | 10/2001 |
| JP | 2003019586 A | * | 1/2003 |
| JP | 02003185424 A | * | 7/2003 |

OTHER PUBLICATIONS

European search report for corresponding application No. 05009904 dated Aug. 28, 2008.

* cited by examiner

METHOD FOR CHECKING A NOZZLE FOR A LASER BEAM MACHINE

The present application is based on and claims priority of Japanese patent application No. 2004-155930 filed on May 26, 2004, the entire contents of which are hereby incorporated by reference.

BACKGROUND OF THE INVENTION

1. Field of the Invention

The present invention relates to a device which checks the shape of a nozzle tip of a laser beam machine for any abnormality (foreign matter, deformation, or tip flaws) using a shape/property recognition device such as a camera.

2. Description of the Related Art

In the case of conventional laser beam machines, predetermined standard machining conditions are registered with an NC system according to material and workpiece thickness.

When laser machining is continued under standard machining conditions, abnormalities of the nozzle attached to the tip of the machining torch can cause machining defects such as generation of dross. To maintain optimum machining conditions, conventionally the operator has to sense anything unusual in advance, stop the machine, check the nozzle, and if any abnormality is recognized, the operator has to replace the nozzle manually, clean the nozzle, correct any deformation, or change machining conditions.

A device is known which can detect any machining defect of workpieces by carrying out imaging of cut portions of the workpieces with a CCD camera (Japanese Patent Laid-Open No. 10-258376, or Patent Document 1).

Any foreign matter attached to the nozzle of the laser beam machine makes it difficult to maintain a fixed clearance between the tip of the nozzle and top face of the workpiece in a stable manner. This will cause machining defects such as degradation of machining quality or even disable machining.

Also, any foreign matter attached to the nozzle tip can cause an outlet in the nozzle tip to go out of round, disturbing flow velocity distribution of jets of assist gas. This will cause machining defects such as degradation of machining quality or even disable machining.

To avoid the above problems and maintain optimum machining is something an unskilled operator cannot accomplish and requires a skilled operator with many years of experience. This has hindered continuous unattended operation from being implemented.

SUMMARY OF THE INVENTION

The present invention provides a nozzle checker for a laser beam machine which solves the above problems.

A laser beam machine according to the present invention comprises, as basic means, a bed, a pallet which is disposed on the bed and holds a workpiece, a column which moves along an X axis, that is, a longitudinal axis of the bed, a saddle which is supported by the column and moves along a Y axis orthogonal to the X axis, and a machining head which is supported by the saddle and moves along a Z axis perpendicular to the plane formed by the X axis and Y axis.

Besides, it comprises means for optically checking a nozzle attached to the tip of a laser machining tool.

The laser machining tool comprises a torch which has optical means including a condenser lens; and a nozzle which is replaceably attached to the tip of the torch.

The means for optically checking a nozzle includes a CCD camera body, a lens, and a lighting device which illuminates the nozzle as well as a device which raises and lowers the means for optically checking a nozzle, in opposing relation to the nozzle.

According to the present invention, since the out-of-roundness of the nozzle is always kept within tolerances, the flow velocity distribution of jets of assist gas is not disturbed and high machining quality can be maintained.

Furthermore, since the nozzle tip is kept free of foreign matter, dents, etc., it is possible to maintain a fixed clearance between the tip of the nozzle and top face of the workpiece in a stable manner and thus maintain high machining quality.

This allows even an unskilled operator to perform high-quality, high-precision machining and even enables continuous unattended operation.

DETAILED DESCRIPTION OF THE PREFERRED EMBODIMENTS

Figure 1:
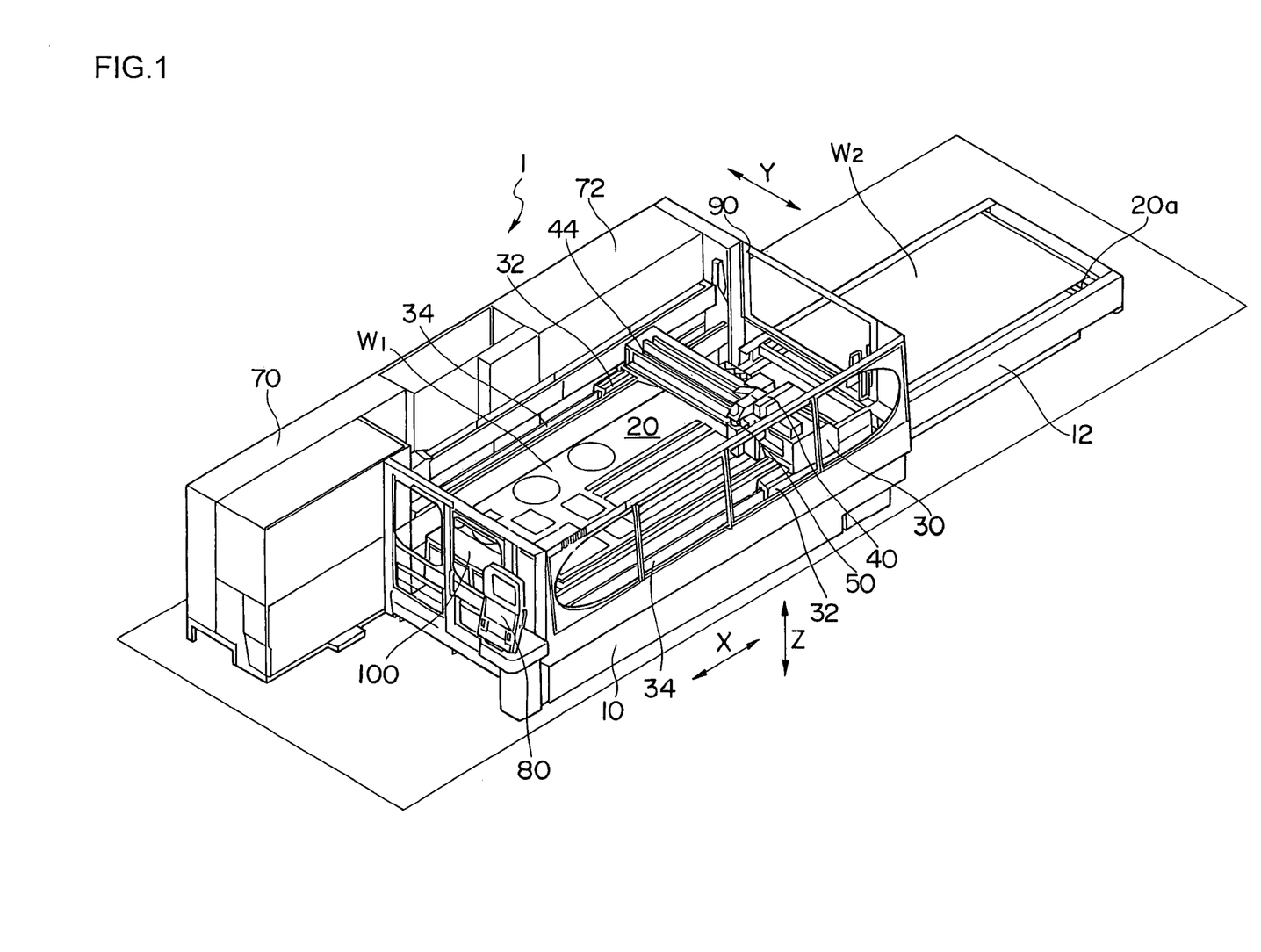
FIG. 1 is a perspective view showing an entire laser beam machine according to the present invention.
Figure 2:
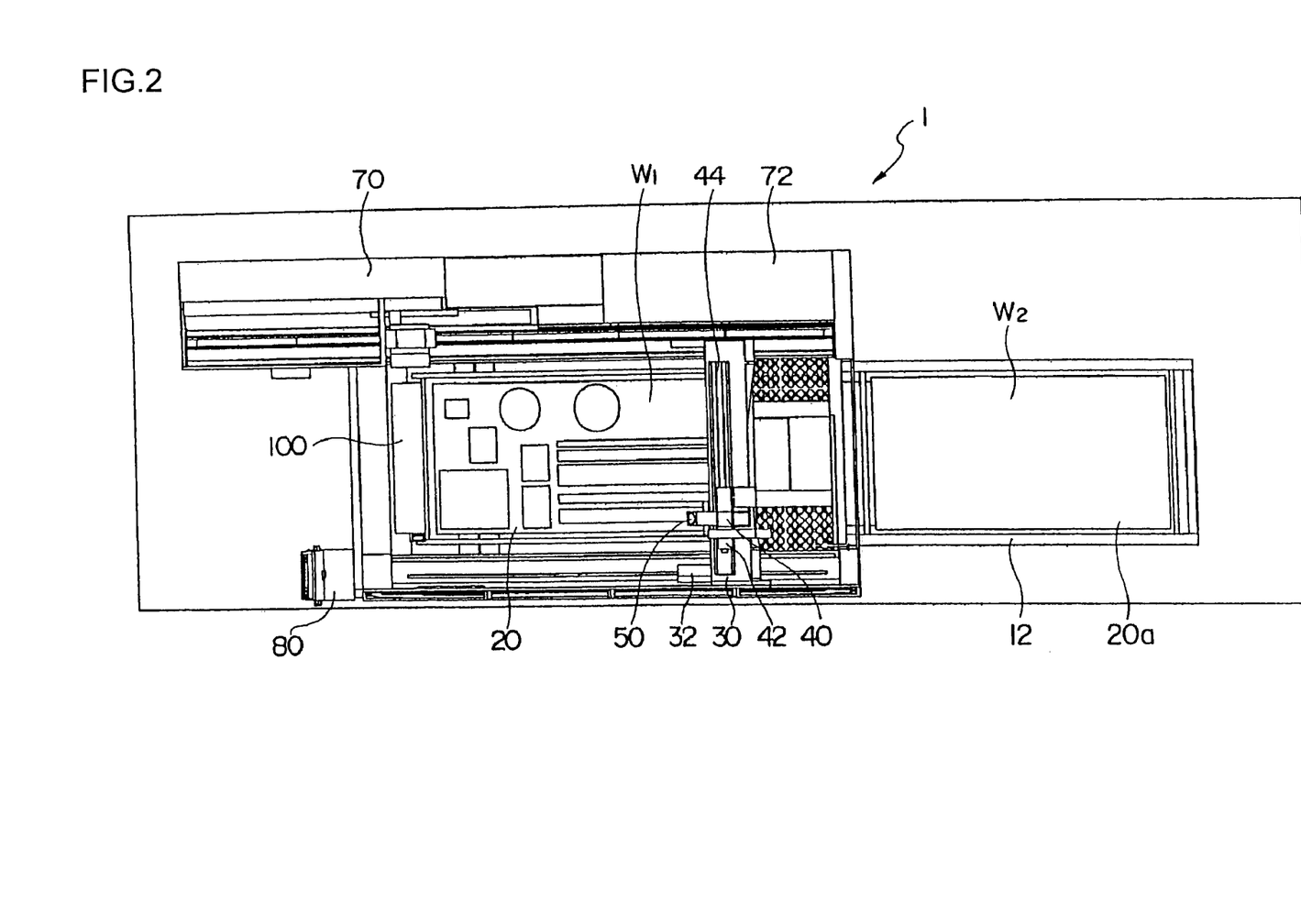
FIG. 2 is plan view of the laser beam machine according to the present invention.
Figure 3:
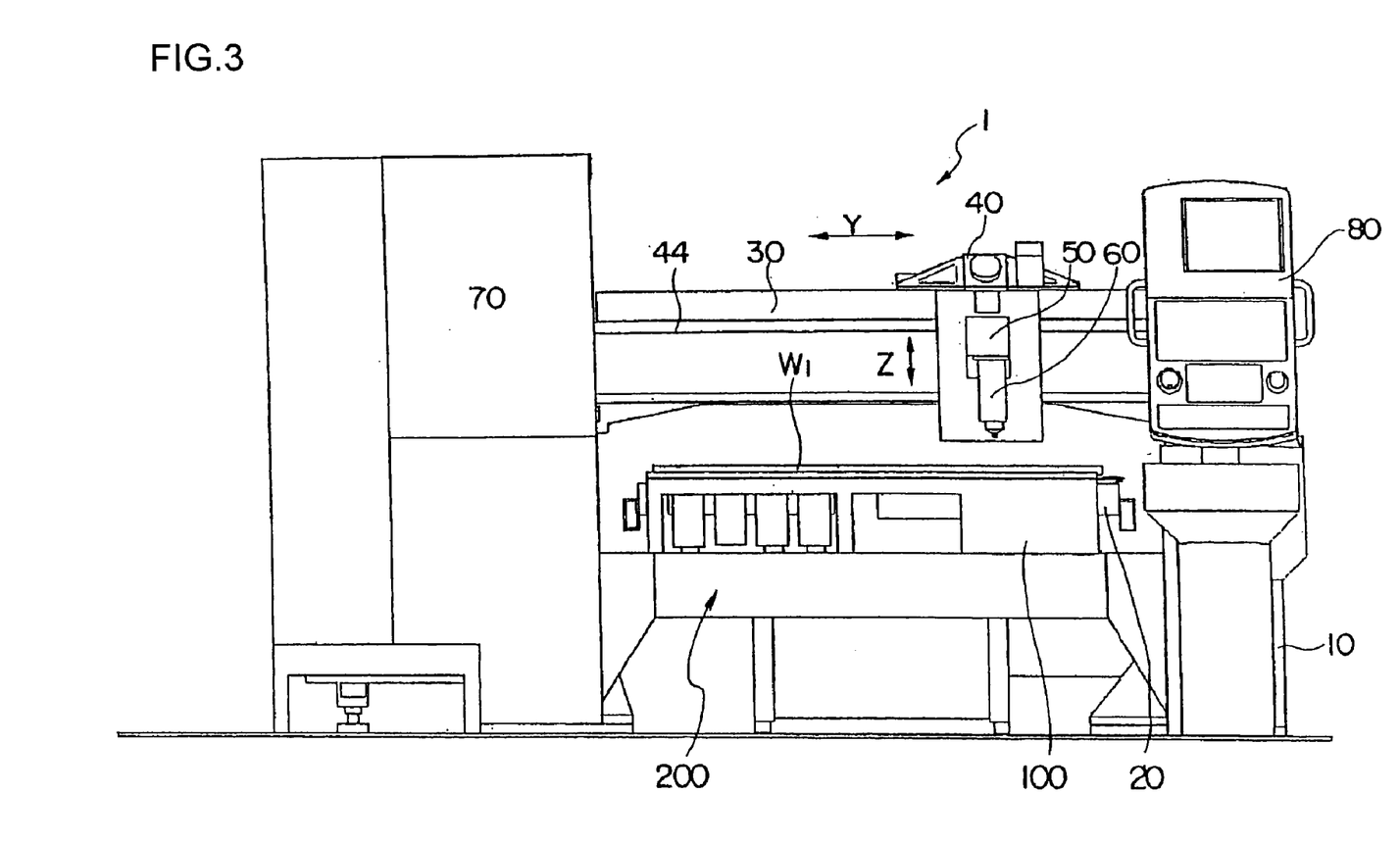
FIG. 3 is a front view of the relevant portion of the laser beam machine according to the present invention.
Figure 4:
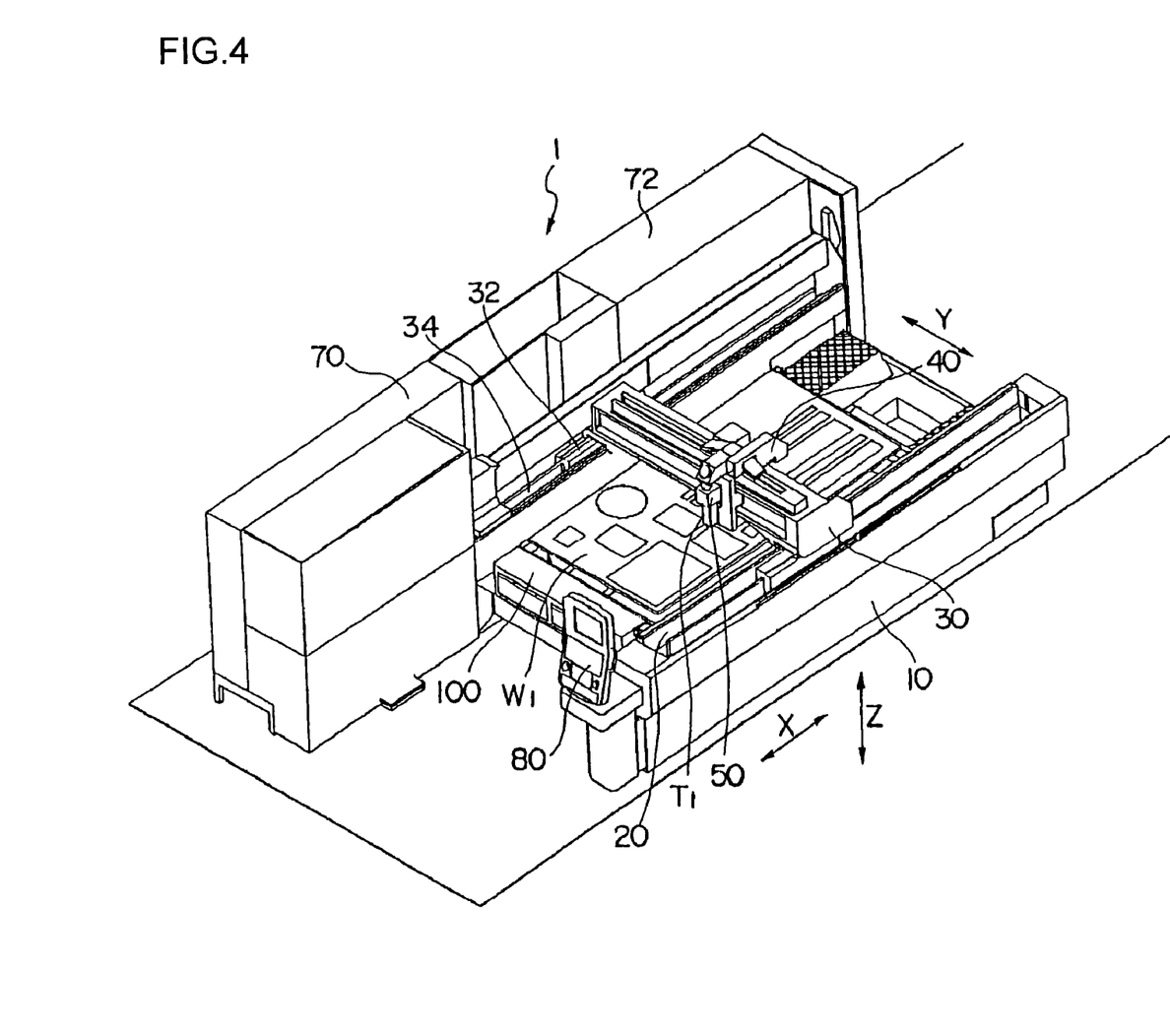
FIG. 4 is a perspective view of the relevant portion of the laser beam machine according to the present invention.
Figure 5:
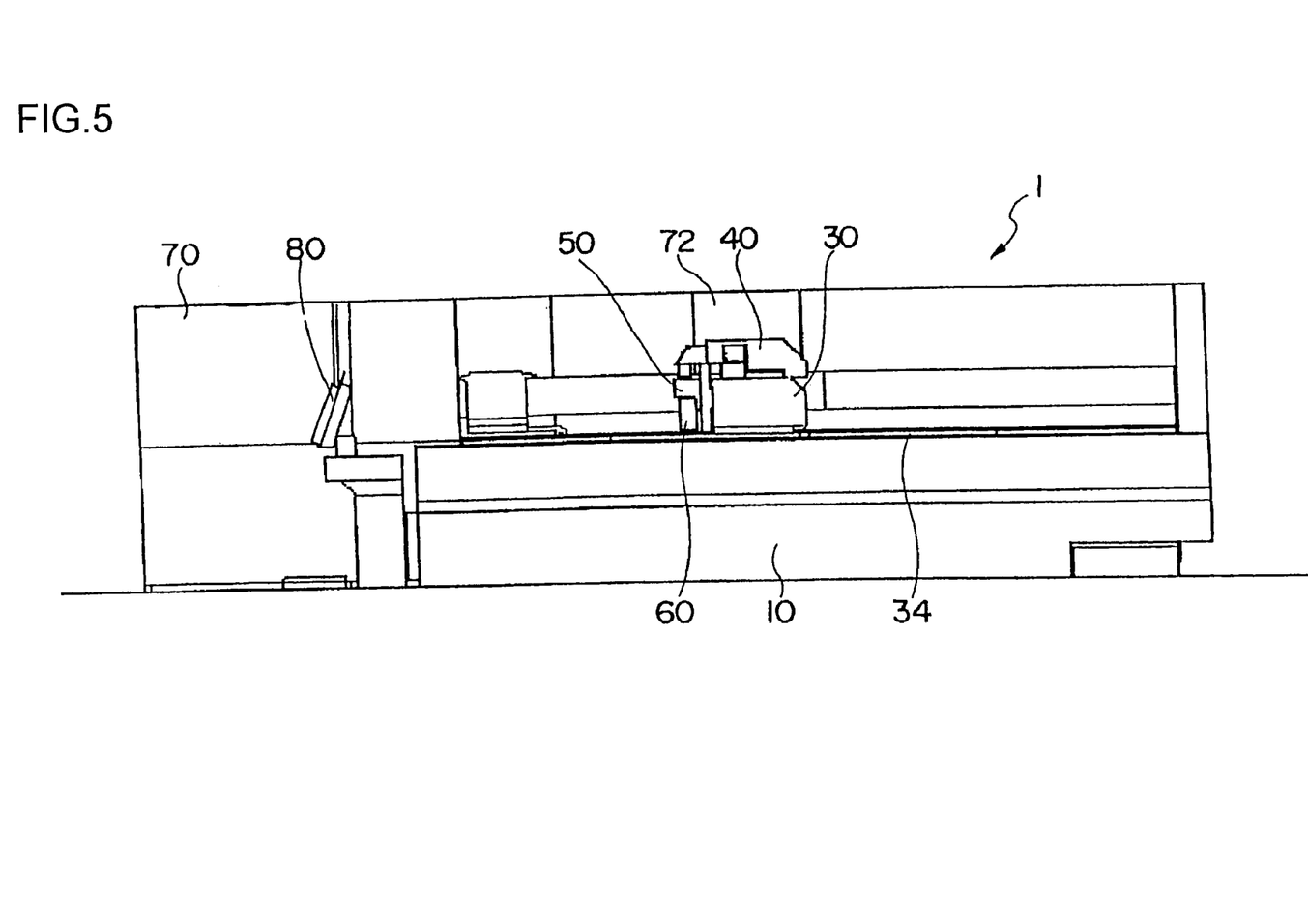
FIG. 5 is a side view of the relevant portion of the laser beam machine according to the present invention.

FIG. 1 is a perspective view showing an overall configuration of a laser beam machine according to the present invention, FIG. 2 is a plan view, FIG. 3 is a front view, FIG. 4 is a perspective view of the relevant portion, and FIG. 5 is a side view.

A laser beam machine, generally denoted by reference number 1, has a pallet (table) 20 which is disposed on a bed 10 to carry a plate-shaped workpiece $W_1$. A pallet changer 12 is placed on the longitudinal extension of the bed 10, and a pallet 20a carrying a workpiece $W_2$ to be machined next is awaiting its turn.

A pair of guide rails 34 are installed on both sides of the bed 10 along its length and a column 30 is mounted on the guide rails 34 in such a way as to be movable along an X axis.

Means for driving the column 30 along the X axis is provided by, for example, a linear motor, which is formed by a stator installed on the guide rails 34 and a moving member installed on a linear-motion guide 32.

A guide rail 44 is installed on the column 30 along a Y axis orthogonal to the X axis and a saddle 40 is mounted in such a way as to be movable along the Y axis. The saddle 40 is equipped with a linear-motion guide 42 which is engaged with the guide rail 44. A linear motor is formed by the guide rail 44 and linear-motion guide 42.

The saddle 40 has a guide rail installed along a Z axis perpendicular to the plane formed by the X axis and Y axis and has a machining head 50 mounted in such a way as to be movable along the Z axis. The machining head 50 has an optical system which admits a laser beam from a laser oscillator 72.

The machining head 50 is equipped replaceably with a laser machining tool 60. A machining area is fitted with a cover 90 to ensure safety. A power panel 70 and the laser oscillator 72 are disposed adjacent to the bed 10. A control panel 80 for use by the operator to give various commands is disposed on a longitudinal end of the bed 10. A setup station 100 for laser machining tools is installed on that end of the bed 10 which is closer to the control panel 80.

Figure 6:
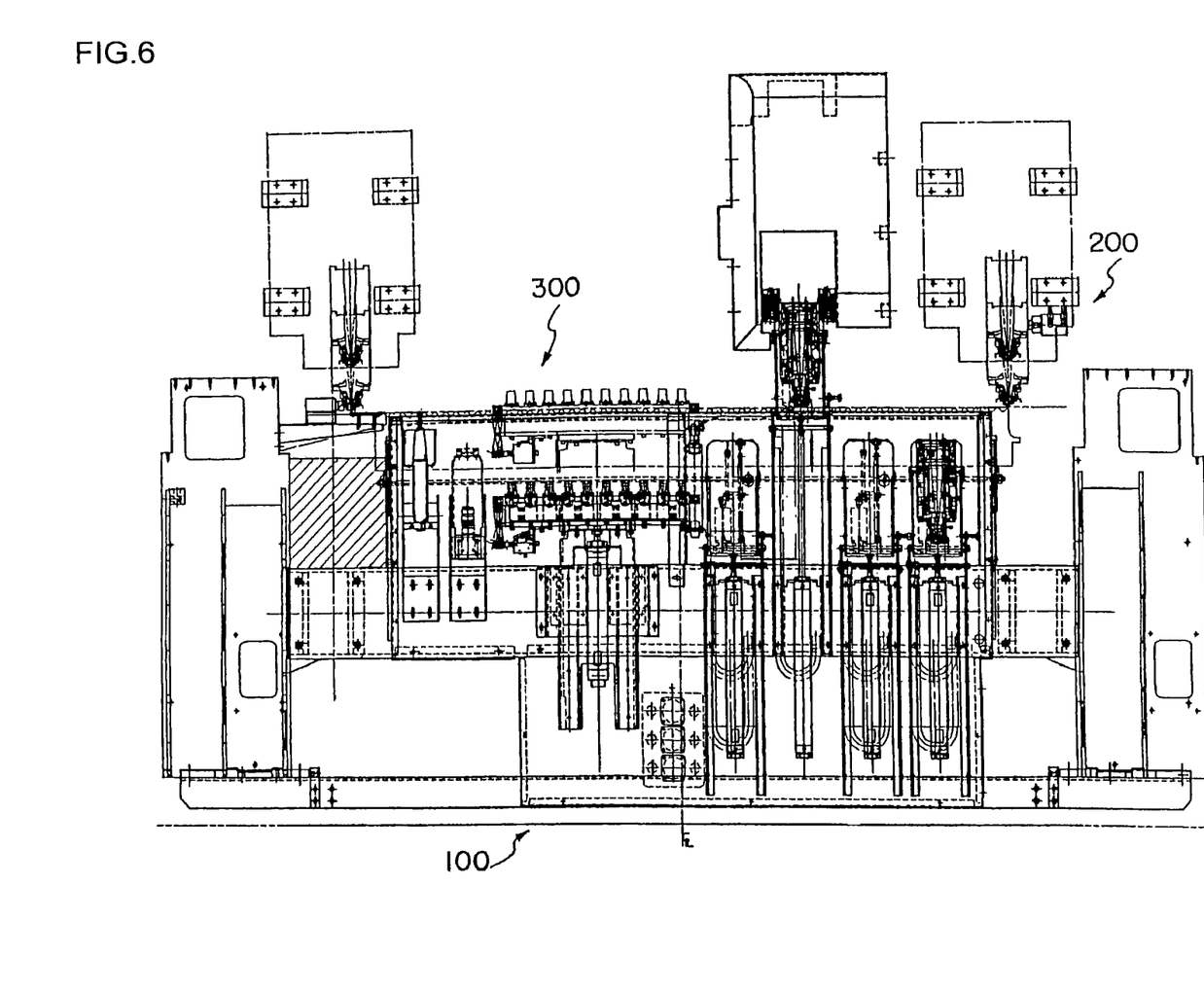
FIG. 6 is a front view of a setup station for laser machining tools.
Figure 7:
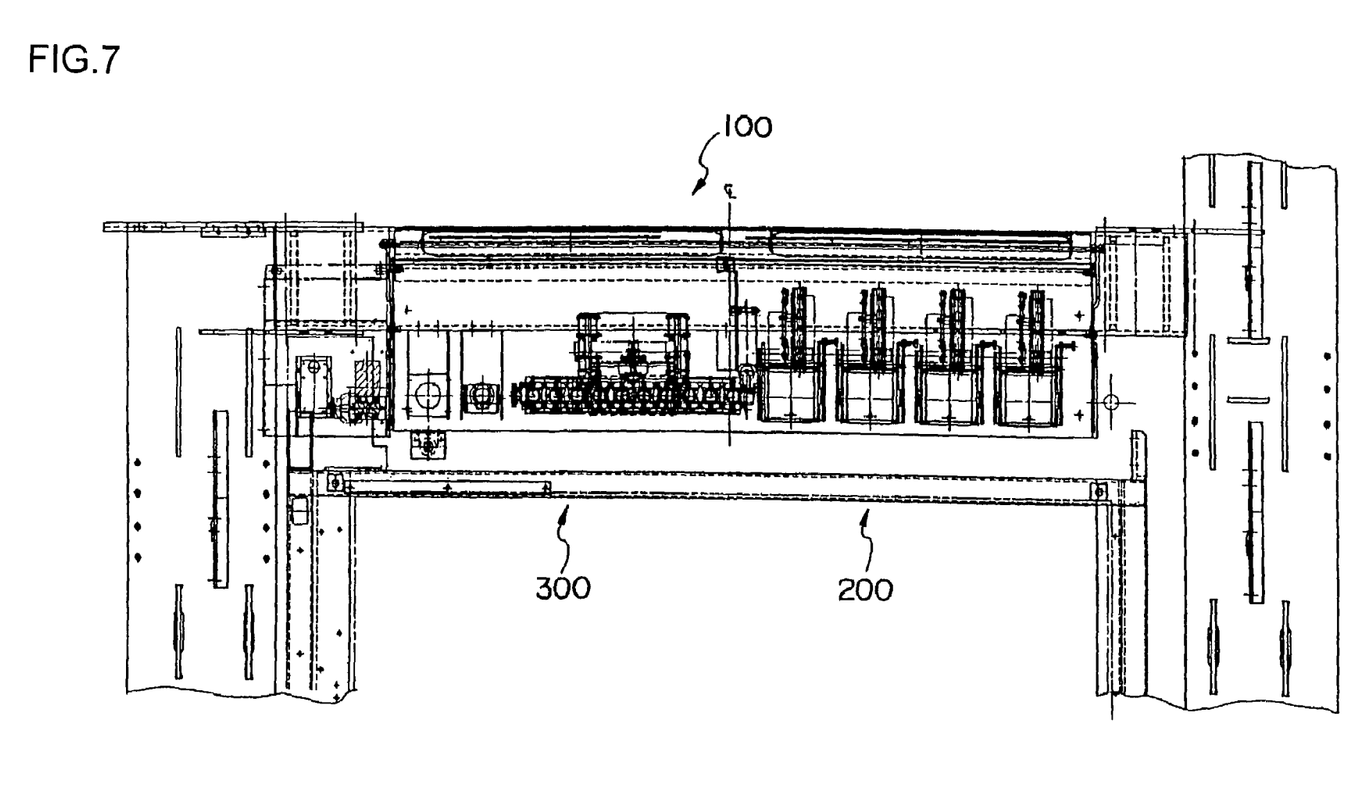
FIG. 7 is a plan view of the setup station for laser machining tools.

FIG. 6 is a front view of the setup station 100 for laser machining tools as viewed from the table and FIG. 7 is a plan view.

The setup station 100 for laser machining tools includes a tool station 200 and nozzle station 300, where the tool station 200 is equipped with a tool change magazine 220 for laser machining tools which in turn are equipped with a torch and nozzle while the nozzle station 300 is equipped with a nozzle change magazine for nozzles of laser machining tools.

Figure 8:
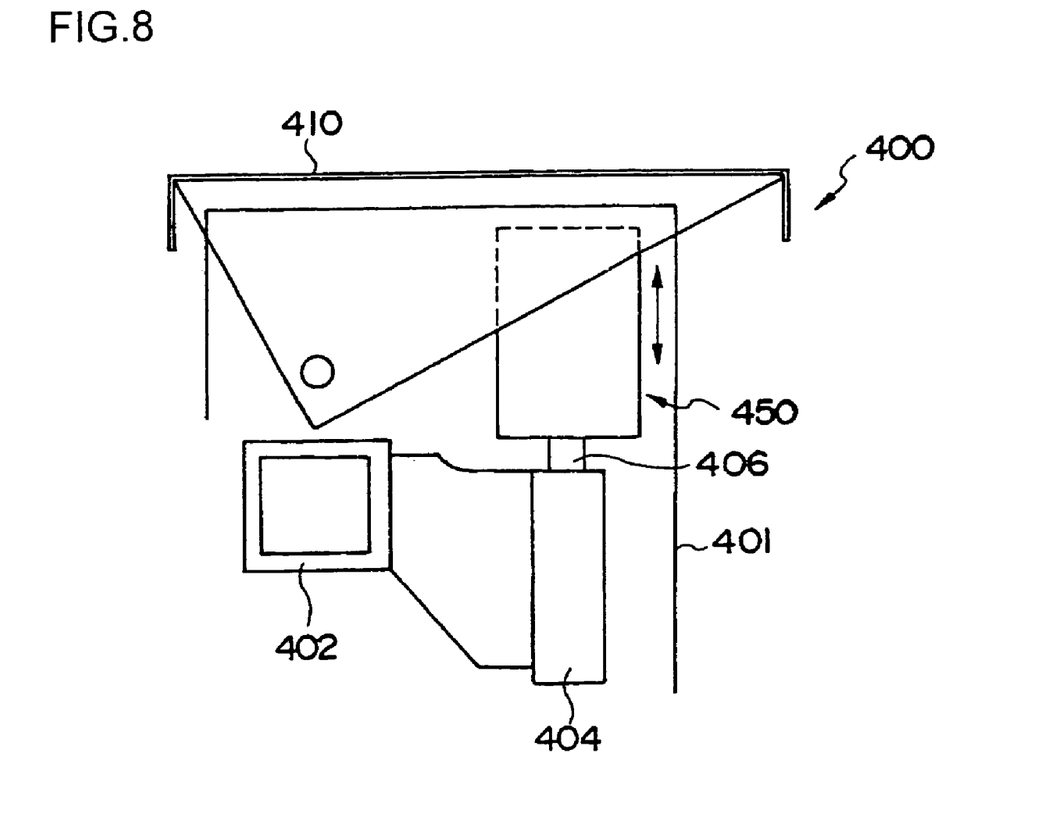
FIG. 8 is an explanatory diagram of a nozzle checker.
Figure 9:
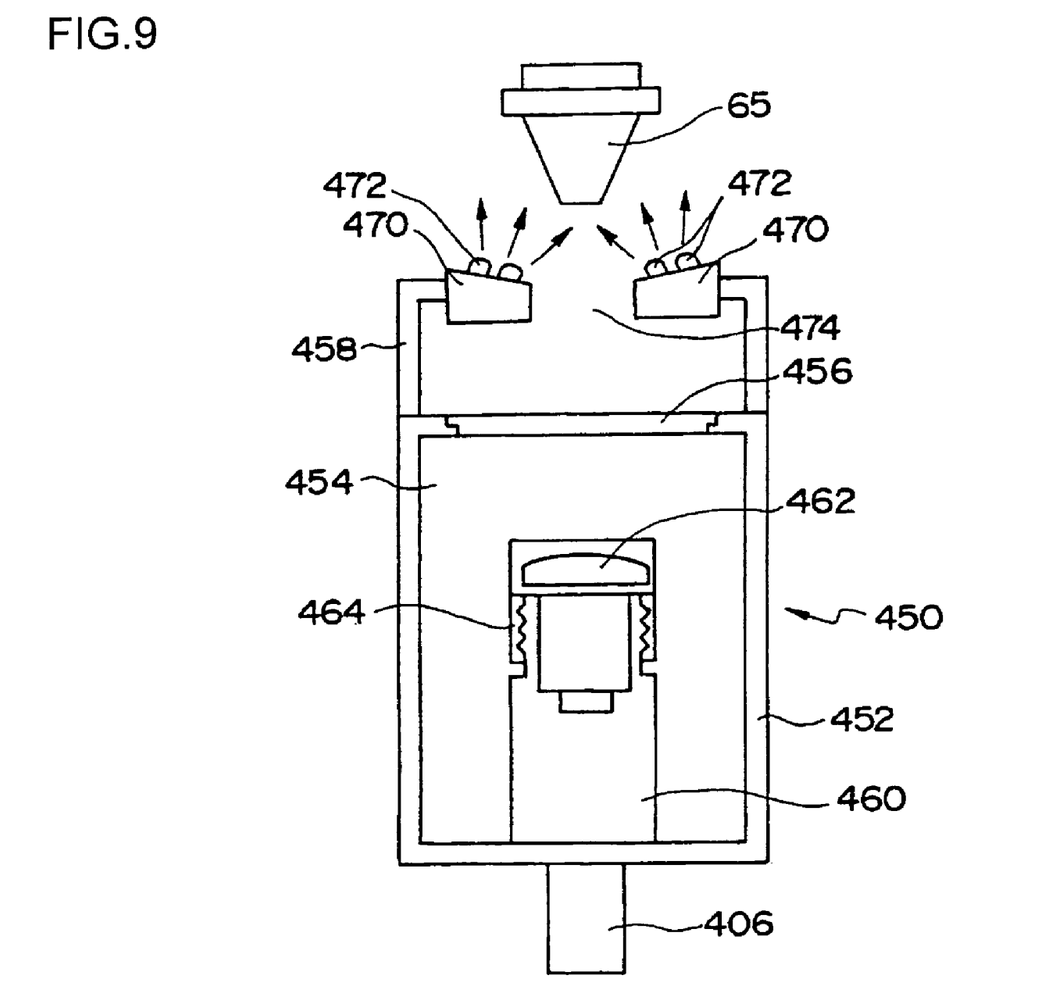
FIG. 9 is an explanatory diagram of a nozzle checker.

FIG. 8 is an explanatory diagram of the nozzle checker according to the present invention. FIG. 9 is an explanatory diagram of a camera unit.

The nozzle checker, generally denoted by reference number 400, is mounted on a base 402 disposed in a cover 401.

A cylinder 404 fixed to the base 402 raises and lowers a piston rod 406. A camera unit 450 is installed on the upper end of the piston rod 406. The camera unit 450 is constantly housed in a cover 401 which prevents intrusion of dust, dirt, and the like. Its upper surface is protected by a cover 410 which covers the entire setup station 100 for laser machining tools.

In order for the nozzle to be checked, the cylinder 404 raises the camera unit 450 using the piston rod 406 to just below the nozzle so that the camera unit 450 will face the nozzle.

The camera unit 450 is equipped with a housing 452 mounted at the tip of the piston rod 406. A CCD camera body 460 is fixed to a camera chamber 454 installed in the housing 452. The CCD camera body 460 has a lens 462, which is mounted in such a way that its distance from a light-receiving surface of the camera is adjustable with an adjustment screw 464.

Top of the camera chamber 454 is covered with protective glass 456 to protect the CCD camera body 460, lens 462, etc. from foreign matter.

A bracket 458 is installed on top of the camera chamber 454 and a ring light 470 is mounted on the bracket 458.

The ring light 470 is equipped with a high-intensity LED 472 and has an opening 474 in the center.

Images of a nozzle 65 illuminated by the ring light 470 are taken by the CCD camera body 460 to check the nozzle 65 optically.

Figure 10A:
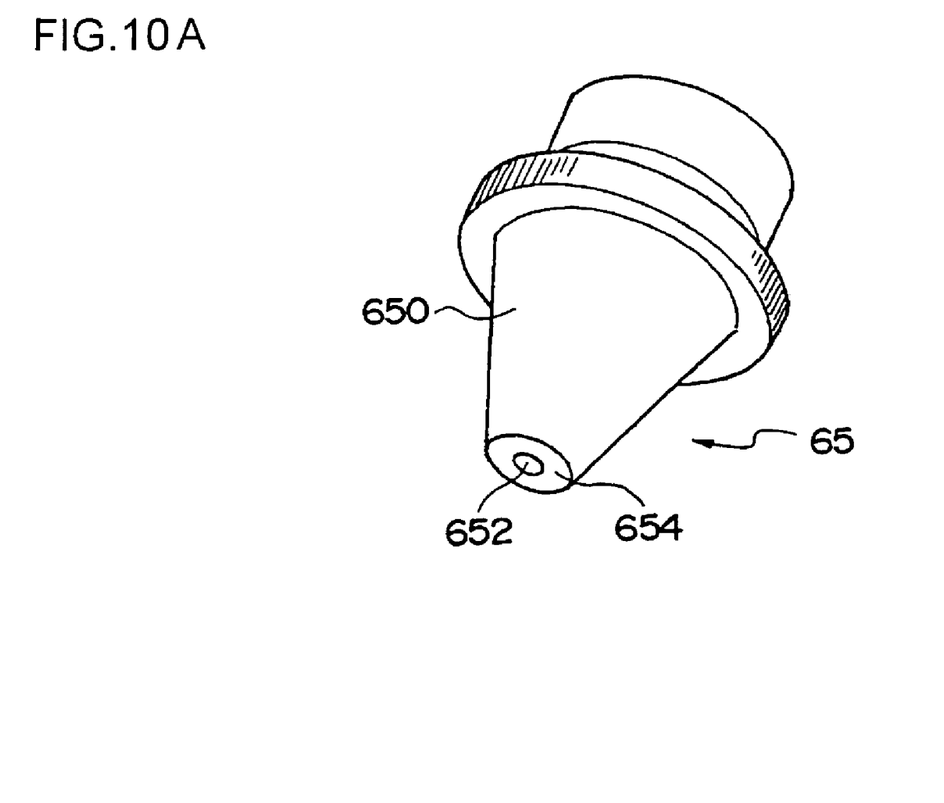
FIG. 10 is an explanatory diagram illustrating a technique for checking a nozzle.

FIG. 10 shows a technique for checking a nozzle with an intelligent nozzle checker according to the present invention.

The nozzle 65 comprises a nozzle body 650 and has a nozzle hole 652 formed in the center of its tip surface 654.

Figure 10B:
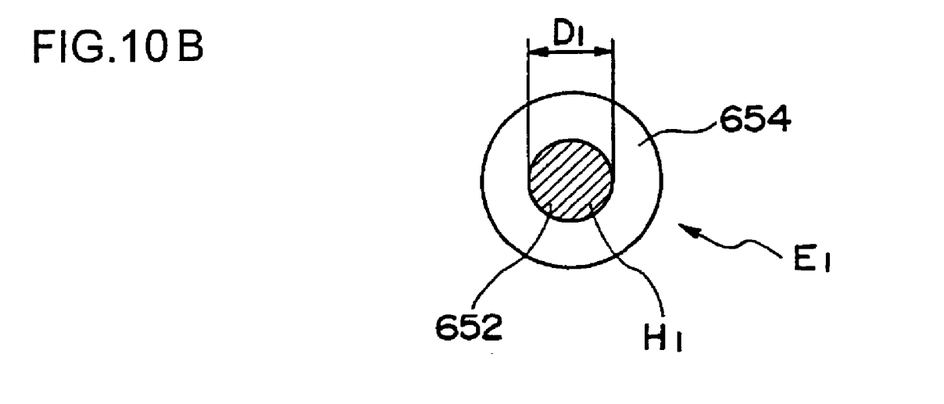

FIG. 10(b) shows a CCD camera image $E_1$ of the tip surface 654 of the nozzle 65. The surface of the tip 654 has normal brightness, and a shadow $H_1$ of the nozzle hole 652 is photographed accurately. By detecting the bore diameter $D_1$ of the nozzle hole 652, it is possible to identify the type of the nozzle 65.

Figure 11A:
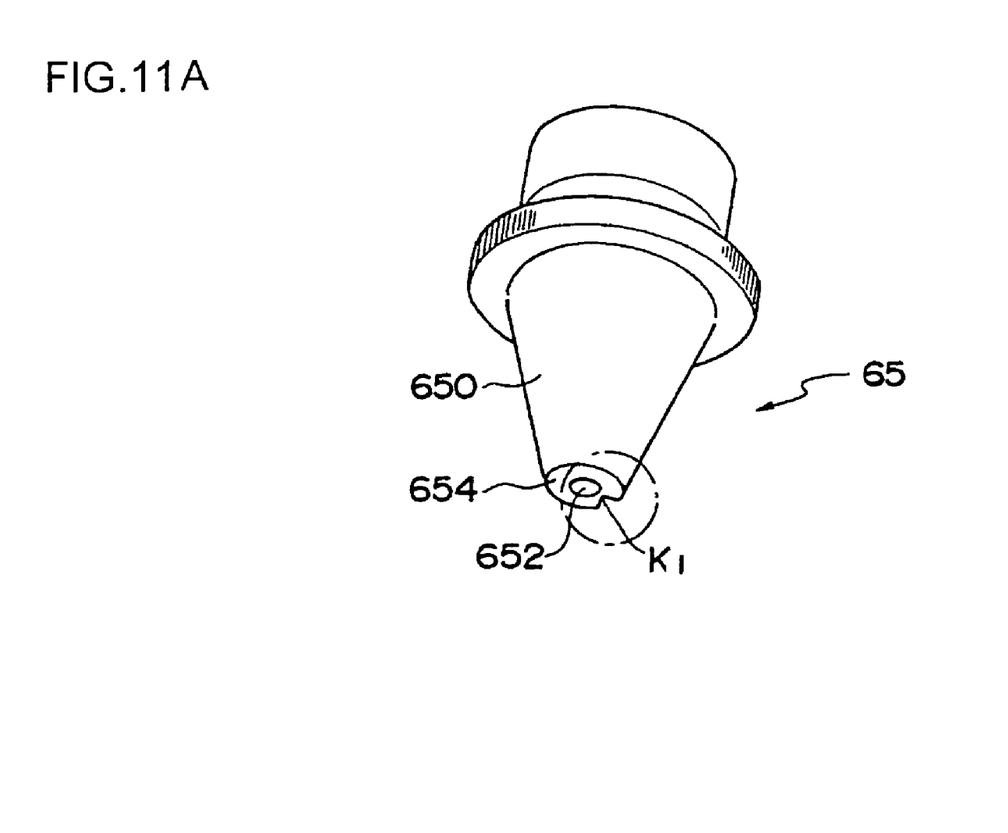
FIG. 11 is an explanatory diagram illustrating an example in which a flaw is produced on a nozzle.
Figure 11B:
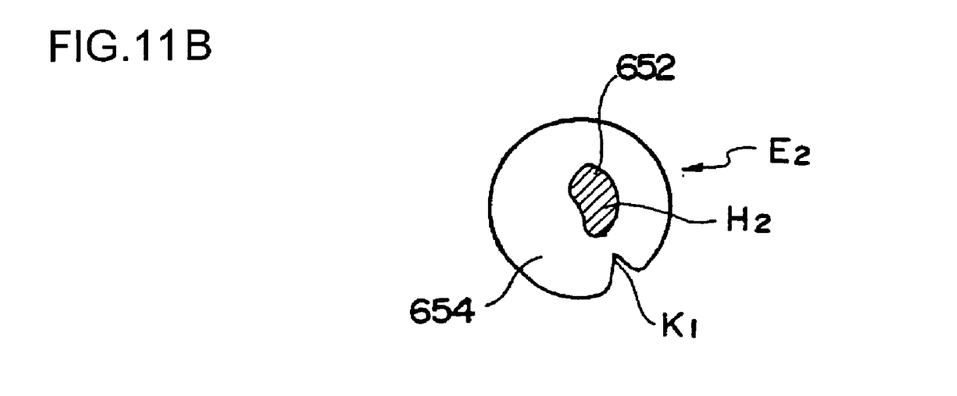

FIG. 11 shows an example in which a flaw $K_1$ is produced on the tip portion of the nozzle 65 for some reason.

The shape of the flaw $K_1$ appears in an image $E_2$ and a shadow $H_2$ of the nozzle hole 652 is deformed.

The image makes it possible to determine that the nozzle is defective.

Figure 12A:
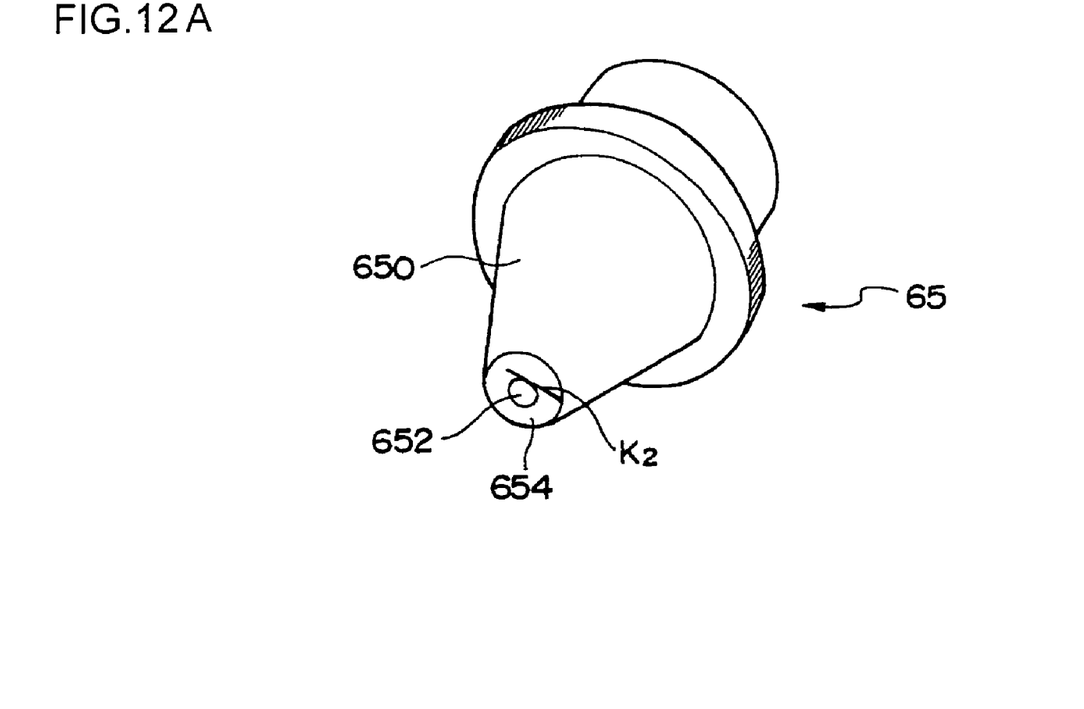
FIG. 12 is an explanatory diagram illustrating an example in which a flaw is produced on a nozzle.
Figure 12B:
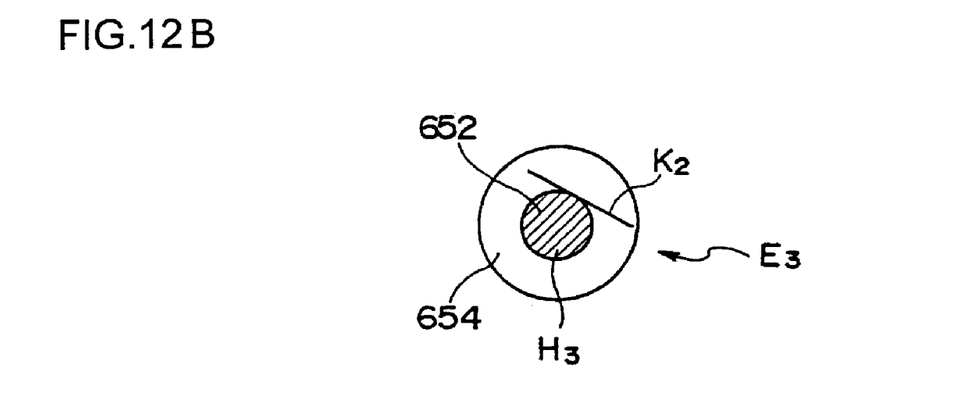

FIG. 12 shows an example in which a flaw $K_2$ is produced on the tip surface 654 of the nozzle 65.

Although a shadow $H_3$ of the nozzle hole 652 appearing in an image $E_3$ is normal, reflected brightness of the tip surface 654 is reduced. Detection of the reduction in the reflected brightness allows the nozzle defect to be detected.

Figure 13A:
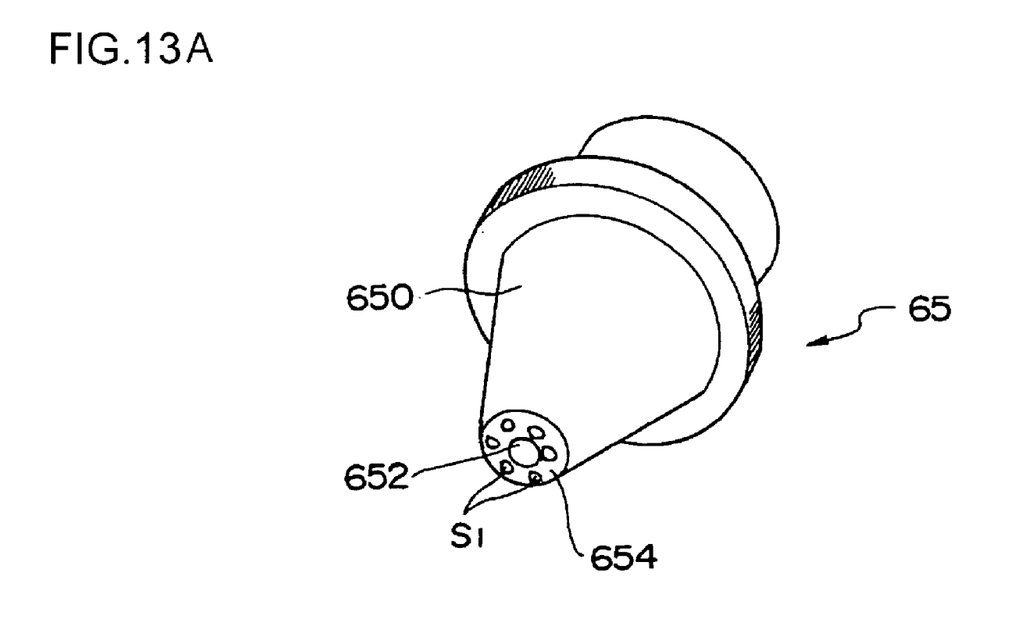
FIG. 13 is an explanatory diagram illustrating an example in which a nozzle is scattered with spatters.
Figure 13B:
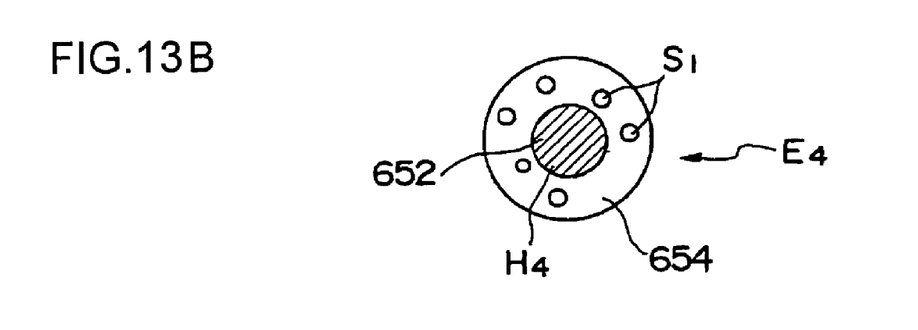

FIG. 13 shows the nozzle tip surface 654 scattered with spatters $S_1$ of work material heated by laser machining.

Although the hole diameter of the nozzle hole 652 appearing in an image $E_4$ is normal, the reflected brightness of the surface is reduced greatly. This phenomenon allows the nozzle defect to be detected.

Figure 14:
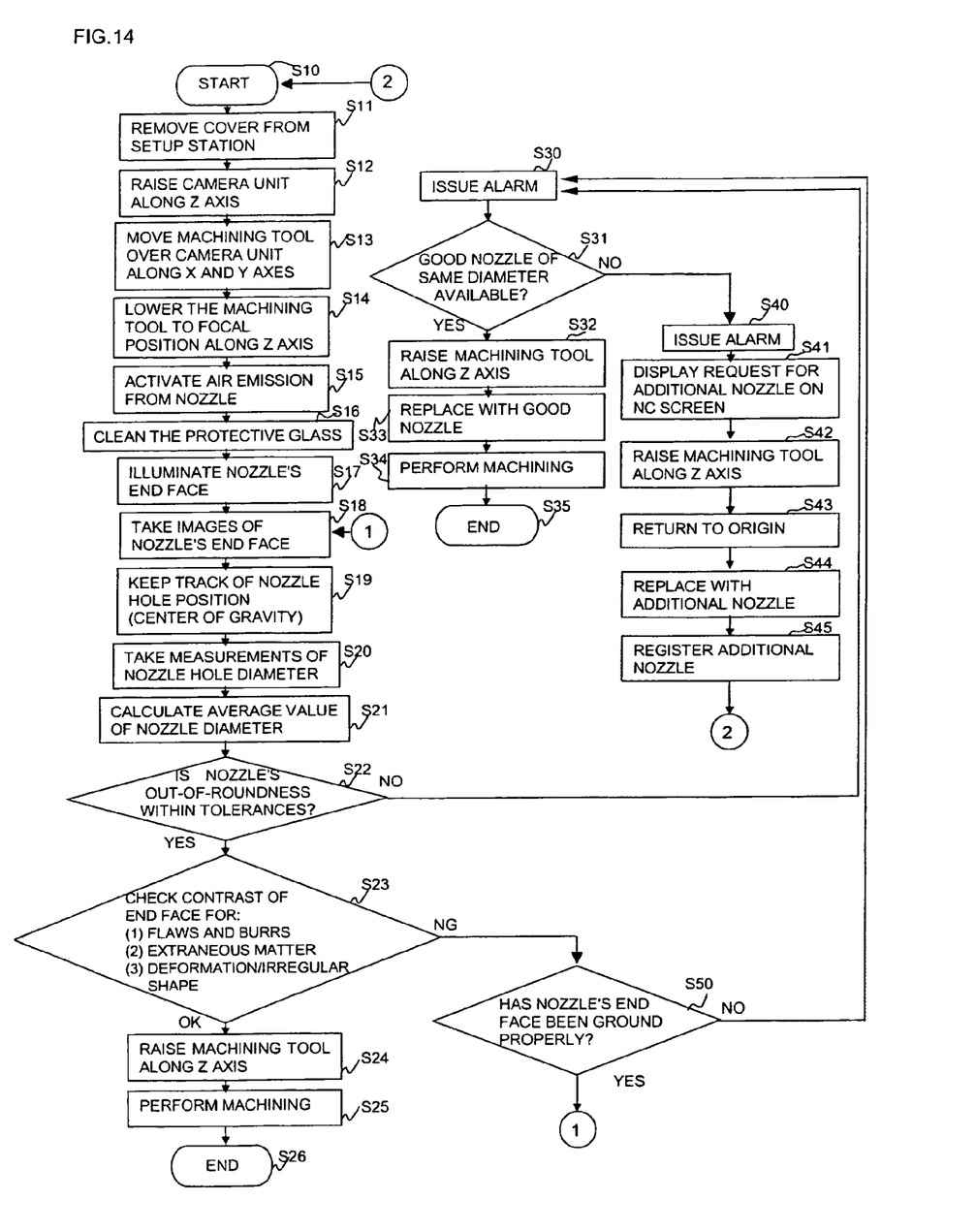
FIG. 14 is a flowchart of a nozzle checking process.

FIG. 14 is a process flowchart of the nozzle checker according to the present invention.

In Step S10, processing is started. In Step S11, the cover is removed from the setup station. In Step S12, the camera unit is raised along the Z axis. In Step S13, the machining tool is moved above the camera unit. In Step S14, the machining tool is lowered to the focal position of the camera.

In Step S15, a jet of air is emitted from the nozzle, and in step S16, the protective glass of the camera unit is cleaned. In Step S17, the lighting of the camera unit is turned on to illuminate the end face of the nozzle. In Step S18, the end face of the nozzle is imaged by the camera.

In Step S19, the center of gravity position of the nozzle hole is calculated by processing image data of the imaged end face of the nozzle. Then, the diameter of the nozzle hole is measured in multiple images in Step S20 and the average value of the nozzle hole is calculated in Step S21.

In Step S22, it is checked whether the calculated out-of-roundness of the nozzle is within tolerances. If it is within tolerances, the nozzle's end face is checked in Step S23 for flaws and burrs, extraneous matter such as spatters, deformation/irregular shape, etc. based on the contrast of its video images.

If the results of the checks are good, the procedure advances to Step S24, where the machining tool is raised and returned from the setup station to the machining area. Then, machining is performed in Step S25 and the processing is finished in Step S26.

If it is found in Step S22 that the out-of-roundness of the nozzle is not within tolerances, an alarm is issued in Step S30 to notify the operator to that effect. In Step S31, it is checked whether there is any good nozzle of the same diameter at the setup station. If one is available, the machining tool is raised in step S32 and the mounted nozzle is replaced with the good nozzle in Step S33.

Machining is performed in Step S34 and the processing is finished in Step S35.

If it is found in Step S31 that there is no good nozzle of the same diameter at the setup station, an alarm is issued in Step S40 to notify the operator to that effect and a request for an additional nozzle is displayed on an NC screen in Step S41.

The machining tool is raised in Step S42 and is returned to the origin in Step S43. Then, in Step S44, the mounted nozzle is replaced with the additional nozzle by the operator. In Step S45, the additional nozzle is registered with a controller. Then, the flow returns to Step S10.

If it is found in Step S23 that the nozzle's end face is not good, it is checked in Step S50 whether the nozzle's end face has been ground properly. If it has been ground properly, the flow returns to Step S18, but if it has not been ground properly, the flow goes to Step S30.

Incidentally, although a linear motor has been cited in the above example as a driving means along the X and Y axes, the present invention can also employ a ball screw.

Also, although a ring light with an opening in the center has been cited in the above example as a lighting device which illuminates the nozzle, the present invention can also employ a halogen light.

What is claimed is:

1. A method for checking a nozzle for a laser beam machine comprising:
    a bed;
    a pallet which is disposed on the bed and holds a workpiece;
    a column which moves along an X axis, that is, a longitudinal axis of the bed;
    a saddle which is supported by the column and moves along a Y axis orthogonal to the X axis; and
    a machining head which is supported by the saddle and moves along a Z axis perpendicular to the plane formed by the X axis and Y axis,
    the method comprising the steps of:
    obtaining image data of the nozzle attached to the tip of a laser machining tool via camera means,
    processing the image data with respect to an end face of the nozzle to calculate a center of gravity position of a nozzle hole at the end face of the nozzle,
    measuring the diameter of the nozzle hole in multiple images from the image data of the nozzle and calculating an average value of the nozzle hole diameter to calculate an out-of-roundness of the nozzle,
    checking whether the calculated out-of-roundness is within tolerances, and
    if the calculated out-of-roundness is within tolerances, performing a machining process, else
    if the calculated out-of-roundness is not within tolerances, replacing the nozzle with a different nozzle.

2. The method according to claim 1, wherein the camera means includes a COD camera body, a lens, and a lighting device which illuminates the nozzle.

3. The method according to claim 1, further comprising mechanically raising and lowering the camera means in opposing relation to the nozzle.

4. The method according to claim 1, further comprising, if the calculated out-of-roundness is within tolerances, checking the nozzle for at least one of defects or extraneous matter based on contrast in the multiple images of the image data.

5. The method according to claim 1, further comprising imaging the nozzle in a setup station, and if the calculated out-of-roundness is within tolerances, moving the nozzle from the setup station to a machining area to perform the machining process.

6. The method according to claim 1, further comprising imaging the nozzle in a setup station, and if the calculated out-of-roundness is not within tolerances, checking whether there is a different nozzle in the setup station having the same diameter as the imaged nozzle, and if so replacing the imaged nozzle with the different nozzle having the same diameter.

* * * * *